ular Pharmacol-
United States Patent [19]

Krapcho et al.

[11] Patent Number: 5,116,851

[45] Date of Patent: May 26, 1992

[54] PHARMACEUTICAL COMPOSITION AND METHOD FOR TREATING CARDIOVASCULAR DISEASES USING SUBSTITUTED ANILIDES AND SULFONAMIDES

[75] Inventors: John Krapcho, Somerset, N.J.; James L. Bergey, Lansdale, Pa.; Gary J. Grover, Stockton, N.J.

[73] Assignee: E. R. Squibb & Sons, Inc., Princeton, N.J.

[21] Appl. No.: 471,254

[22] Filed: Jan. 26, 1990

[51] Int. Cl.⁵ .................. A01N 43/00; A01N 43/60; A01N 41/06; A01N 37/18
[52] U.S. Cl. ........................... 514/354; 514/255; 514/601; 514/613; 514/617; 514/608; 564/182
[58] Field of Search ............... 514/599, 354, 613, 614, 514/629, 255, 601, 617

[56] References Cited

U.S. PATENT DOCUMENTS 3,378,586 4/1968 Krapcho ..................... 564/182
4,724,235 2/1988 Shanklin et al. .................. 514/212

FOREIGN PATENT DOCUMENTS 0300865 1/1989 European Pat. Off. .

OTHER PUBLICATIONS

*Advances in Drug Research,* vol. 16, (Jan. 1987), pp. 379-386, R. A. Janis et al.
G. J. Grover et al., *Journal of Cardiovascular Pharmacology,* 14:331-340 (Feb. 1989).
J. Krapcho et al., *Compounds Related to Thiazesim. III,* vol. 11, pp. 361-364, Mar. 1968.

*Primary Examiner*—Frederick E. Waddell
*Assistant Examiner*—T. J. Criares
*Attorney, Agent, or Firm*—Theodore R. Furman, Jr.

[57] ABSTRACT

A novel pharmaceutical composition and method is disclosed for the treatment of cardiovascular diseases, e.g. myocardial ischemia and/or arrhythmia. The method and composition include an effective amount of a compound of the formula

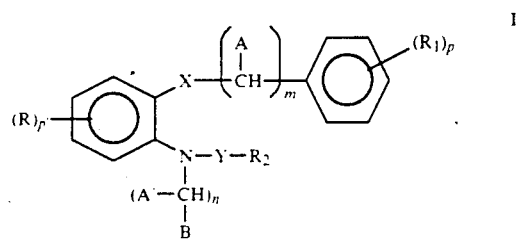

wherein X, Y, R, $R_1$, A, A', m, n, p, p' and B are as defined herein.

38 Claims, No Drawings

PHARMACEUTICAL COMPOSITION AND METHOD FOR TREATING CARDIOVASCULAR DISEASES USING SUBSTITUTED ANILIDES AND SULFONAMIDES

BACKGROUND OF THE INVENTION

Myocardial ischemia is the reduction of blood flow to cardiac tissue which can result in cell death (infarction) and dysrhythmic conditions, e.g. ventricular arrhythmia and ventricular fibrillation.

Certain calcium channel blockers and thromboxane receptor antagonists have been identified as anti-ischemic agents by their ability to reduce infarct size. Many calcium antagonists also possess cardiodepressant activity, i.e. they reduce contractile function. This is of importance since cardiodepression in patients with coronary insufficiency may further compromise hearts possessing low functional reserve. Accordingly, certain calcium channel blockers are contraindicated in patients with poor myocardial function.

In an effort to optimize treatment for patients with ischemic heart disease, anti-ischemic agents can be evaluated in terms of an ischemic selectivity which can be viewed as a ratio of cardioprotection to cardiodepression. Anti-ischemic agents which provide a satisfactory level of cardioprotection with minimal cardiodepression would be a useful addition to the art.

SUMMARY OF THE INVENTION

In accordance with the present invention a method for the treatment of cardiovascular diseases, e.g. myocardial ischemia and ventricular arrhythmia is disclosed. This method comprises administering, to a patient in need thereof, an effective amount of a compound having the formula

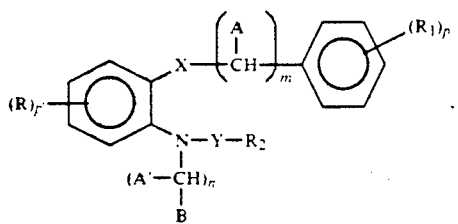

and to acid addition salts thereof, wherein

R and $R_1$ each independently represent hydrogen, halo, lower alkyl, lower alkoxy, trihalomethyl, nitro, amino or hydroxy;

X represents oxa (—O—) or thia (—S—);

B represents a basic nitrogen-containing radical of less than 12 carbon atoms;

A and A' are independently selected from hydrogen or lower alkyl;

m is zero or an integer from 1 to 3;

n represents 2-5;

p and p' can be the same or different integer from 1 to 3;

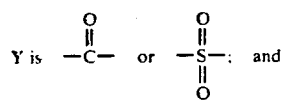

Y is $-\overset{O}{\underset{\|}{C}}-$ or $-\overset{O}{\underset{\underset{O}{\|}}{\overset{\|}{S}}}-$; and $R_2$ is lower alkyl, aryl, aralkyl, cycloalkyl(lower alkyl), lower alkenyl, lower alkadienyl, α-substituted phenyl alkyl, aralkenyl, aralkynyl or heteroaryl.

DETAILED DESCRIPTION OF THE INVENTION

The compounds of formula I have been found to be a selective class of anti-ischemic agents which, advantageously, also possess anti-arrhythmic activity. Thus, the method of the present invention can be for treating ischemia and arrhythmia separately or together. The compounds of formula I possess both calcium channel blocking and sodium blocking activities. By virtue of this calcium channel blocking activity, the compounds of formula I may be employed in the various indications for which calcium channel blockers are known to be useful, such as for angina and other cardiovascular diseases. (See for example, R. A. Janis et al., *Advances in Drug Research*, Vol. 16, p. 379-386 (1987) which is incorporated herein by reference.) Unexpectedly, in assessing the cardiodepressant and cardioprotective qualities of the compounds of formula I, it has been found that this class of compounds is significantly more cardioprotective than cardiodepressant. That is, the present method is able to provide a significant reduction in infarct size and arrhythmia while depressing cardiac function only minimally when compared to the calcium channel blocker, diltiazem.

The term lower alkyl as used herein refers to straight and branched chain saturated aliphatic groups containing up to 10 carbon atoms, such as methyl, ethyl, propyl, isopropyl, butyl, iosbutyl, t-butyl, amyl, isoamyl, hexyl and the like. Methyl and ethyl are preferred. The lower alkoxy groups contain alkyl groups of the same character attached to the oxygen atoms.

The term "aryl" refers to phenyl and substituted phenyl. Exemplary substituted phenyl groups are phenyl groups substituted with 1, 2 or amino (—$NH_2$), alkylamino, dialkylamino, nitro, halogen, hydroxyl, trifluoromethyl, alkyl (of 1 to carbon atoms), alkoxy (of 1 to 4 carbon atoms), alkylthio (of 1 to 4 carbon atoms), alkanoyloxy, carbonyl or carboxyl groups.

The term "heteroaryl" refers to an aromatic heterocyclic group having at least one heteroatom in the ring. Preferred groups are pyridinyl, pyrrolyl, imidazolyl, furyl, thienyl, oxazolyl or thiazolyl.

The term "cycloalkyl" refers to groups having 3, 4, 5, 6 or 7 carbon atoms.

Each of the four halogens is contemplated by the terms "halo" and "trihalomethyl," but in the case of the halogens themselves chlorine and bromine are preferred while trifluoromethyl is the preferred trihalomethyl group.

Exemplary —Y—$R_2$ groups include lower alkanoyl (e.g., acetyl, propionyl, butyryl and the like), cycloalkyl-loweralkanoyl (e.g., cyclohexylacetyl), lower alkenoyl (e.g., 2-butenoyl, 2-pentenoyl), lower alkadienoyl (e.g., sorboyl), aralkanoyl (e.g., phenyl-lower alkanoyl such as phenacetyl), α-substituted phenylacetyl (e.g., α-acetoxyphenyl acetyl), aralkenoyl (e.g., phenyl-lower alkenoyl such as cinnamoyl), aralkynoyl (e.g., phenyl-lower alkynoyl such as phenyl propioloyl), aroyl (e.g., benzoyl and R-benzoyl, such as p-chlorobenzoyl, trimethoxybenzoyl and the like), heteroaroyl (e.g., pyridoyl), lower alkane sulfonyl (e.g., methanesulfonyl), aralkyl sulfonyl (e.g., benzyl sulfonyl) and aryl sulfonyl (e.g., benzenesulfonyl).

The basic nitrogen containing radicals symbolized by B include the following radicals

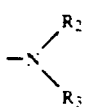
II wherein $R_3$ and $R_4$ independently represent hydrogen, lower alkyl, hydroxy-lower alkyl, R substituted-phenyl-lower alkyl, R substituted cinnamyl (e.g. p-methoxy cinnamyl), 2- or 4-pyridylalkyl, and N-(lower alkyl)-phenyl-(lower alkyl) forming such basic groups as amino, lower alkylamino, e.g., methylamino, ethylamino, di(lower alkyl)amino, e.g., dimethylamino, diethylamino, dipropylamino, (hydroxy-lower alkyl)amino, e.g., hydroxy-ethylamino, (di(hydroxy-lower alkyl)-amino, e.g., di(hydroxyethyl)amino, phenyl(-lower alkyl) amino, e.g.,benzylamino, phenethylamino and the like.

In addition the nitrogen may join with the groups represented by $R_3$ and $R_4$ to form a 5 to 7 membered monocyclic heterocyclic containing, if desired, an oxygen or an additional nitrogen atom, (no more than two hetero atoms altogether). The heterocyclic group may also be substituted by one to three of the following: lower alkyl, lower alkoxy, hydroxy-lower alkyl, lower alkanoyloxylower alkyl.

Thus, heterocyclic groups represented by B include, for example, piperidino, (lower alkyl)piperidino, e.g., 2-methylpiperidino, (lower alkoxy)piperidino, e.g., 4-methoxypiperidino, pyrrolidino, (lower alkyl)pyrrolidino, e.g., 2-methylpyrrolidino, 3-methylpyrrolidino, di(lower alkyl)pyrrolidino, e.g., dimethylpyrrolidino, morpholino, piperazino, (lower alkyl)-piperazino, e.g., $N^4$-methylpiperazino, 2-methylpiperazino or 3-methylpiperazino, di(lower alkyl)-piperazino, e.g., 2,3-dimethylpiperazino, hydroxy-lower alkylpiperazino, e.g., 4-hydroxyethylpiperazino, (lower alkoxy)piperazino, e.g., 2-ethoxypiperazino, (lower alkanoyloxy)-lower alkylpiperazino, e.g., 4-(2-acetoxyethylpiperazino), hexamethyleneimino and homopiperazino.

The bases of Formula I form acid addition salts by reaction with the common inorganic and organic acids. Such inorganic salts as the hydrohalides, e.g., hydrobromide, hydrochloride, hydroiodide, sulfates, nitrates, phosphates, etc., and organic salts as acetate, oxalate, tartrate, maleate, citrate, succinate, benzoate, ascorbate, salicylate, theophyllinate, camphorsulfonate, alkanesulfonate, e.g., methanesulfonate, or arylsulfonate, e.g., benzenesulfonate, toluenesulfonate and the like are also within the scope of the invention. Physiologically acceptable acids are, of course, employed where the salt form is prepared for therapeutic use, but the salts may also be used in the purification and isolation of the product.

Preferred compounds are those wherein
R is hydrogen, methoxy or Cl;
$R_1$ is hydrogen, methoxy or Cl;
A is hydrogen or methyl;
A' is hydrogen or methyl;

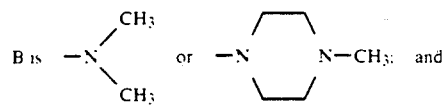

—Y—$R_2$ is phenylacetyl or cinnamoyl.
Most preferred are those compounds wherein
R is hydrogen;
$R_1$ is methoxy;
A and A' are each hydrogen;
m, p and p' are each 1;
n is 3;

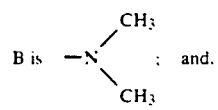

—Y—$R_2$ is phenylacetyl.

U.S. Pat. No. 3,378,586 to Krapcho describes the method for the preparation of the compounds of formula I and those methodologies are incorporated herein by reference. Such methodology for compounds of formula I wherein n is 2 or 3 involve reacting a compound of the formula

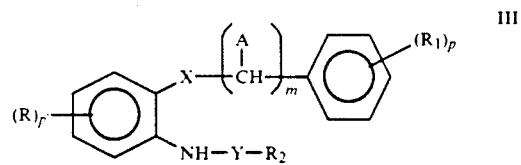
III with a compound of the formula

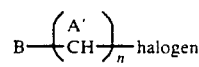
IV in the presence of a strong base such as an alkali metal amide (e.g., sodium amide), powdered alkali metal hydroxide (e.g, sodium hydroxide), or an alkaline metal hydride (e.g., sodium hydride).

Compounds of formula III can, in turn, be prepared by acylating a compound of the formula

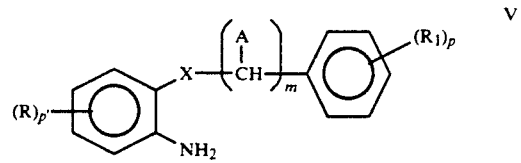
V using known techniques, e.g., with an acyl halide, acid anhydride or reacting the free acid with the amine in the presence of condensing agents such as dicyclohexylcarbodiimide.

Alternatively, compounds of formula V can be reacted with compounds of formula IV and thereafter acylated to provide the compounds of the present invention.

Compounds of formula V can, in turn, be prepared by either reacting a nitrophenol or nitrothiophenol of the formula

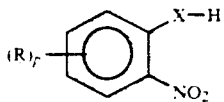

with a compound of the formula

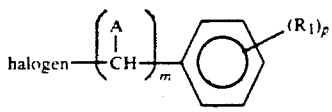

and thereafter reducing the nitro group by standard techniques, e.g., treating with stannous chloride or, for compounds where X is —S—, the reaction may be carried out by substituting the corresponding amino compound of formula VI for the nitro compound in which case the reduction step is omitted.

Compounds of the present invention where n is 4 or 5 can be prepared by reacting a compound of the formula

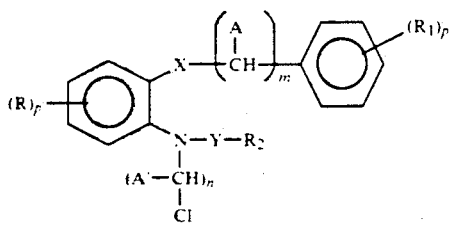

with a compound of the formula

HB                                          IX to provide compounds of formula I.

Compounds of formula VIII are, in turn, provided by reacting a compound of the formula

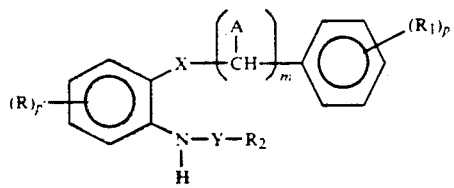

with a compound of the formula

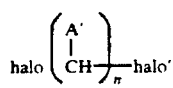

wherein halo and halo' can be the same or different halogen.

Compounds of formula X are, in turn, provided by reacting a compound of formula V, above, with Cl—Y—R$_2$                                  XIII Arrhythmias contemplated for treatment by the present method will include, but are not limited to, ventricular arrhythmias arising from various pathologies of the heart such as myocardial infarction, myocardial ischemia, coronary vasospasm, angina at rest, stress induced angina with or without S-T segment elevation, valvular prolapse, and/or reperfusion arrhythmias arising from translumenal angioplasty or coronary bypass and graft, or a clot dissolution with streptokinase, TPA or other suitable therapeutic means for restoring or improving blood flow to the ischemic myocardium. These agents will also be used in the treatment of atrial arrhythmias against which class I agents are known to be effective.

In the present method for treatment of myocardial ischemia and/or arrhythmia, the compounds of formula I may also be used in combination with other agents used in the clinical management of ischemic heart disease and/or heart failure. These agents may include various angiotensin converting enzyme (ACE) inhibitors such as captopril, fosinopril, zofenopril, and enalopril; calcium-entry blockers such as diltiazem, nifedipine or verapamil; nitro vasodilators such as nitroglycerin, isosorbide and nicorandil; beta adrenoceptor blocking agents such as nadolol, propranolol, sotolol and metoprolol; cardiac glycosides such as digitalis; and thromboxane A$_2$ receptor antagonists.

The compounds of formula I can be formulated for use in the present methods in compositions such as tablets, capsules or elixirs for oral administration, or in sterile solutions or suspensions for parenteral administration. The compounds of formula I may also be administered via transdermal patch or nasal inhalation solutions. About 10 to 500 milligrams of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Grover et al., "Dissociation of Cardiodepression from Cardioprotection with Calcium Antagonists: Diltiazem Protects Ischemic Rat Myocardium with a Lower Functional Cost as Compared with Verapamil and Nifedipine", Journal of Cardiovascular Pharmacology, pages 331–340, Vol. 14, No. 2 (1989), have developed a methodology for assessing the efficacy of calcium channel blockers in ischemia! Grover et al. express the efficacy of anti-ischemic agents as the ratio of lactate dehydrogenase (LDH) release versus preischemic, post-drug cardiac function. Lactate dehydrogenase is an enzyme released in the heart during an ischemic event and is an index of cardiac cell necrosis. In the Grover et al. model, this is measured during reperfusion and an agent which provides for lower release levels of LDH is considered to offer greater cardioprotection since lower LDH indicates a smaller infarct size. Cardiac function is determined using the double product (DP) of heart rate times the left ventricular developed pressure (LVDP) divided by 1,000.

The lower the value for DP before ischemia for a given agent, the more cardiodepressant it is considered to be. A ratio of LDH release (or cardioprotection) to preischemia cardiac function (DP) is indicative of the ischemic selectivity of the compound, the lower ratios corresponding to the more desirable anti-ischemic agents.

We have examined cardioprotection and cardiodepression for diltiazem, nifedipine and verapamil and determined that diltiazem had the greatest ischemic selectivity. In the following Example, compounds of formula I and diltiazem were evaluated using the techniques described therein.

EXAMPLE 1

N-[2-[[(4-Chlorophenyl)methyl]thio]phenyl]-N-[3-(dimethylamino)propyl]benzeneacetamide A. 2-[(4-Chlorophenyl)methyl]thio]benzenamine A solution of 52.0 g (0.8 mol) of potassium hydroxide (approx. 85%) in 700 ml of ethanol was stirred, cooled to 5°, and treated dropwise with a solution of 100 g (0.8 mol) of 2-aminobenzenethiol in 100 ml of ethanol over a period of 15 minutes while maintaining the temperature at 5°-10°. After stirring for 30 minutes without cooling, the mixture was cooled to 5° and treated dropwise with a solution of 131 g (0.82 mol) of 4-chlorobenzyl chloride (m.p. 25°-27°) in 100 ml of ethanol over a period of 30 minutes while maintaining the temperature at 5°-10°. Potassium chloride slowly precipitated from the mixture. The latter was then refluxed for 3 hours, cooled, filtered and the filtrate was concentrated under reduced pressure. The residue was dissolved in 200 ml of ether, extracted with 50 ml of water and dried over magnesium sulfate. This mixture was filtered, the filtrate was evaporated and the residue was distilled to give 173.7 g of the title A compound as a pale yellow distillate, b.p. 143°-145° (0.1 mm). The material solidified on cooling, m.p. 32°-34°.

Analysis calc'd for $C_{13}H_{12}NClS$: C, 62.51; H, 4.84; N, 5.61; Cl, 14.10; S, 12.84; Found: C, 62.38; H, 4.81; N, 5.63; Cl, 14.26; S, 12.67.

B. N-[2-[[(4-Chlorophenyl)methyl]thio]phenyl]-benzeneacetamide

A stirred solution of 13.4 ml (0.1 mol) of phenylacetyl chloride (98%) was cooled to 5° and treated dropwise with a solution of 25.0 g (0.1 mol) of the title A compound, 14.0 ml (0.1 mol) of triethylamine and 100 ml of chloroform during a period of 25 minutes. The cooling bath was removed and the solution was refluxed for one hour, cooled and extracted with 100 ml of water and then with 30 ml of water. The organic phase was dried over magnesium sulfate, filtered and the solvent evaporated to give a granular product. The latter was suspended in 200 ml of hexane, cooled and filtered to give 34.0 g of the title B compound as a colorless product, m.p. 100°-101°. After crystallization from 70 ml of $CH_3CN$, the colorless material weighed 31.8 g; m.p. 101°-103°. $R_f$ 0.75 (1:1 ethyl acetate-hexane, vis UV, PMA + heat).

Analysis calc'd for $C_{21}H_{18}NClOS$: C, 68.56; H, 4.93; N, 3.81; Cl, 9.64; S, 8.72; Found: C, 68.47; H, 5.00; N, 3.55; Cl, 9.42; S, 8.44.

C. N-[2-[[(4-Chlorophenyl)methyl]thio]phenyl]-N-[3-(dimethylamino)propyl]benzeneacetamide A stirred solution of 26.0 (0.07 mol) of the title B compound in 400 ml of toluene was treated with 3.45 g (0.072 mol) of sodium hydride (50% oil dispersion). This mixture was slowly heated to 80° C. and maintained at that temperature for 15 minutes. Thereafter, the mixture was heated at 100° C.-105° C. for 20 minutes, cooled to 20° C. and treated with 40 ml (0.086 mol) of 2.15N 3-dimethylaminopropyl chloride in toluene. After heating at 105°-110° for 5 hours, the mixture was cooled and extracted with 75 ml of water. The organic phase was added portionwise to a cold solution of 23 ml of 6N hydrochloric acid in 200 ml of water. The mixture was shaken and the resulting emulsion was clarified by the portionwise addition of 75 ml of methanol. The aqueous phase was separated and the organic phase was extracted twice with 25 ml of water. The aqueous phases were combined and treated portionwise with 25 g of potassium carbonate to give an oily product which then became granular. The mixture was extracted with 200 ml of ethyl acetate. The layers were separated and the aqueous phase was extracted twice with 100 ml of ethyl acetate. The organic phases were combined, dried over anhydrous magnesium sulfate, filtered and the solvent evaporated to give 28.7 g of a pale yellow oil. The latter was treated with 100 ml of hexane, warmed and then cooled and filtered to give 23.3 g of the title compound as a nearly colorless solid, m.p. 92°-94°. After recrystallization from 20 ml ethyl acetate −60 ml hexane, the colorless solid weighed 22.0 g; m.p. 94°-96°. Recrystallization of 17.9 g of this material from 20 ml of isopropanol gave 16.4 g of the title compound as a colorless solid, m.p. 95°-97°. $R_f$ 0.67 (7:2:1 i—PrOH—NH$_4$OH—H$_2$O, vis. UV, PMA + heat).

Analysis calc'd for $C_{26}H_{29}N_2ClOS \cdot \frac{1}{4}H_2O$: C, 6B.25; H, 6.50; N, 6.12; Cl, 7.75; S, 7.00; Found: C, 67.97; H, 6.50; N, 6.08; Cl, 7.83; S, 6.88.

EXAMPLE 2

N-[3-(Dimethylamino)propyl]-N-[2-[[(4-methoxyphenyl)methyl]thio]phenyl]benzeneacetamide, monohydrochloride A. 2-[(4-Methoxybenzy-1)thio]aniline A stirred solution of 62.6 g (0.5 mol) of 2-aminobenzenethiol in 350 ml of 90% ethanol was treated with 22.0 g (0.55 mol) of sodium hydroxide and stirring was continued until most of the sodium hydroxide was consumed (temperature rose gradually to ∼40°) as the sodium salt of the thiol partially separated. The mixture was cooled to 25°, 86.0 g (0.55 mol) of p-anisyl chloride (prepared by treating 4-methoxybenzyl alcohol with concentrated hydrochloric acid as described in *Org. Synth.*, Coll. Vol. IV, p. 576) was added dropwise (the temperature rose to 45° during the addition), and heated at 72°-73° for 1 hour. On cooling to room temperature, a crystalline product began to separate.

After standing overnight, a large mass of crystalline solid was present. Ethyl acetate (500 ml) was added and the mixture was stirred until the product had dissolved. Water (150 ml) was then added to dissolve sodium chloride and the layers were separated. The organic phase was washed with water (2×100 ml) and the combined organic layers were dried over magnesium sulfate and concentrated on a rotary evaporator. When most of the ethyl acetate had been removed, the product separated as a heavy oil. The mixture was poured into a 1 liter Erlenmeyer flask and 500 ml of hexane was added. On rubbing and stirring, the oily material crystallized. After cooling overnight, the pale yellow solid was filtered, washed with hexane, and dried in vacuo (91.5 g); m.p. 65°-67°. A portion (25 g) was distilled to give 22.3 g (67%) of a light yellow oil which solidified on cooling; b.p. 174°-178° at 0.2 mm; m.p. 66°-68°.

Analysis calc'd for $C_{14}H_{15}NOS$: C, 68.53; H, 6.16; N, 5.71; S, 13.07; Found: C, 68.43; H, 6.41; N, 5.70; S, 13.10.

B. N-[2-[[(4-Methoxyphenyl)methyl]thio]phenyl]benzeneacetamide

The title A compound (26.8 g, 0.11 mol) was added to 14.5 ml of a solution of 0.11 mol of phenylacetyl chloride in 135 ml of chloroform in the presence of 15.3 ml (0.11 mol) of triethylamine. The reaction was carried out as described in Example 1, part B, to give 35.1 g of nearly colorless solid; m.p. 83°–86° (s, 79°). Crystallization from 70 ml of MeCN yielded 32.1 g of the title B compound as a colorless solid; m.p. 94°–96° (s, 91°). TLC: R_f 0.52 (1:1 ethyl acetatehexane; visualized UV, PMA + heat).

Analysis calc'd for $C_{22}H_{21}NO_2S$: C, 72.69; H, 5.82; N, 3.85; S, 8.82; Found: C, 72.64; H, 5.92; N, 3.70; S, 8.81.

C. N-[3-(Dimethylamino)propyl]-N-[2-[[(4-methoxyphenyl)methyl]thiophenyl]benzeneacetamide, monohydrochloride To a stirred suspension of the title B compound (18.2 g; 0.05 mol) in 250 ml of toluene was added 2.5 g (0.052 mol) of 50% sodium hydride. The mixture was heated to 100° C. and refluxed for 15 minutes, cooled to 25° C. and treated with 30 ml of a 2.15 N toluene solution of 3-dimethylaminopropyl chloride to give 22.2 g of a light yellow oil. A sample of the base gave an oily hydrogen chloride salt which solidified when rubbed under ether in the presence of a trace of water.

All of the base in 70 ml of 95% ethanol was treated with 4.2 ml of concentrated hydrochloric acid and diluted to 600 ml with ether to precipitate the hydrogen chloride salt as an oil. Since the latter solidified very slowly on seeding and rubbing, 3 ml of water was added and the mixture was stirred in an ice bath for 45 minutes with occasional rubbing; all of the material solidified. After cooling overnight, the colorless solid was filtered, washed with ether, and dried in vacuo (20.9 g); m.p. 136°–139° (bubbles), s. 132°.

The material was purified further as follows: 20.6 g was dissolved in 60 ml of boiling isopropyl alcohol, cooled to 35°, and diluted to 250 ml with ether; the product partly oiled out. On adding 2 ml of water, seeding, stirring, and rubbing, the material solidified. The mixture was diluted further with ether to 450 ml and cooled overnight (20.0 g); m.p. 137°–140°, s, 133°.

The material (19.8 g) was pulverized, suspended in 50 ml of water, cooled for 1 hour, filtered very slowly, washed with cold water (2×10 ml), and air-dried, then in vacuo overnight to provide 14.3 g of the title product; m.p. 147°–150° (bubbles), s. 143°.

Analysis calc'd for $C_{22}H_{32}N_2O_2S \cdot HCl \cdot 0.25H_2O$: C, 66.23; H, 6.90; N, 5.72; Cl, 7.24; S, 6.55 Found: C, 66.19; H, 6.89; N, 5.91; Cl, 7.44; S, 6.29.

EXAMPLE 3

N-[3-(Dimethylamino)propyl]-N-[2-[(phenylmethyl)thio]phenyl]benzeneacetamide, monohydrochloride A. 2-(Benzylthio)phenylacetanilide (Benzylthio)aniline (21.5 g, 0.1 mol) (the preparation of which has been described in Example 1 of U.S. Pat. No. 3,378,586) was reacted with 13.4 ml (0.1 mol) of phenylacetyl chloride in 135 ml of chloroform in the presence of 14.0 ml (0.1 mol) of triethylamine in the manner described under Example 1, part B, to give a solid residue. The latter was redissolved in 35 ml of warm chloroform and diluted with 150 ml of hexane. On seeding and rubbing, a crystalline solid gradually separated. After cooling overnight, the colorless solid was filtered, washed with hexane, and air-dried (22.3 g), m.p. 81°–83°. Following recrystallization from 350 ml of hexane, the title A material weighed 20.8 g, m.p. 82°–84°.

Analysis calc'd for $C_{21}H_{19}NOS$: C, 75.64; H, 5.74; N, 4.20; S, 9.62; Found: C, 75.65; H, 5.77; N, 4.10; S, 9.51.

B. N-[3-(Dimethylamino)propyl]-N-[2-[(phenylmethyl)thio]phenyl]benzeneacetamide, monohydrochloride A stirred solution of 16.7 g (0.050 mol) of the title A compound in 250 ml of toluene was treated first with 2.5 g (0.052 mol) of 50% sodium hydride, then with 30 ml (0.064 mole) of a 2.15N toluene solution of 3-dimethylaminopropyl chloride, as described in part C of Example 2 above, to give 18.4 g of a yellow oil. The base (18.1 g) in 60 ml of isopropyl alcohol was treated with a warm solution of 3.9 g of oxalic acid in 30 ml of isopropyl alcohol; the oxalate salt separated as a gum which readily crystallized on seeding, rubbing, and warming to form a voluminous precipitate. After cooling overnight, the solid was filtered, washed with isopropyl alcohol and with ether, and dried in vacuo (19.8 g), m.p. 159°–162° (bubbles); s, 154°. Following crystallization from 700 ml of MeCN, the colorless material weighed 14.3 g, m.p. 167°–169° (bubbles); s. 162°. R_f 0.77 (7:2:1 i—PrOH—NH_4OH—H_2O: vis. UV, PMA + heat).

Analysis calc'd for $C_{26}H_{30}N_2OS \cdot C_2H_2O_4 \cdot 0.5H_2O$: C, 64.96; H, 6.42; N, 5.41; S, 6.20; Found: C, 64.84; H, 6.35; N, 5.48; S, 5.97.

A stirred suspension of 12.1 g of the oxalate salt in 12.0 ml of water was layered over with the 120 ml of ether and treated portionwise with 6 g of potassium carbonate. When 2 clear layers were obtained they were separated and the aqueous phase was extracted with ether (3×60 ml). The combined organic layers were dried over magnesium sulfate and the solvent evaporated, finally at 0.2 mm, to give 10.4 g of oily base. The latter was dissolved in 75 ml of isopropyl alcohol, treated with 4.7 ml of 5.3N ethanolic hydrochloric acid and 1 ml of water, and diluted with 750 ml of ether. The hydrogen chloride salt separated as a gum which slowly crystallized on seeding and rubbing. Crystallization was expedited by adding approximately 2 ml more water and stirring in an ice-bath for 1 hour. After cooling overnight, the colorless, non-hygroscopic solid was filtered, washed with ether, and dried in vacuo (10.5 g), m.p. 79°–82° (bubbles); s, 76°. The IR spectrum indicated a hydrate. Since the Cl analysis was slightly high, the bulk of this material (9.7 g) was suspended in 20 ml of water, cooled for 1 hour in an ice bath, filtered and washed with 3 ml of cold water (3X). The entrained water was removed in a vac. desiccator and the resulting dry colorless solid was pulverized, suspended in 100 ml of ether and filtered to give 8.0 g of the title compound as a colorless solid, m.p. 74°–77° (s. 70°). R_f 0.68 (7:2:1 i—PrOH—NH_4OH—H_2O; vis UV, PMA + heat).

Analysis calc'd for $C_{26}H_{30}N_2OS \cdot HCl \cdot H_2O$: C, 66.01; H, 7.03; N, 5.92; Cl, 7.50; S, 6.78; Found: C, 66.28; H, 7.03; N, 5.96; Cl, 7.80; S, 6.63.

EXAMPLE 4

N-[2-(Dimethylamino)ethyl]-N-[2-[(phenylmethyl)thio]phenyl]benzeneacetamide, monohydrochloride The title A compound of Example 3 above (16.7 g, 0.050 mol) was treated first with 2.5 g. (0.052 mol) of 50% sodium hydride then with 32 ml (0.075 mol) of a 2.35N toluene solution of 2-dimethylaminoethyl chloride as described in part C of Example 2 above.

The light yellow oily base (18.4 g) was dissolved in 100 ml of butanone and treated with 8.4 ml of 5.45N ethanolic hydrochloric acid. On seeding, the crystalline hydrogen chloride salt separated. After cooling overnight, the colorless solid was filtered, washed with butanone and with ether, and dried in vacuo (14.5 g). m.p. 179°–181° (s, 175°). Following recrystallization from 100 ml of isopropyl alcohol, the title compound as a colorless solid weighed 12.9 g. m.p. 180°–182°. TLC: $R_f$ 0.69 (7:2:1 i—PrOH—NH$_4$OH—H$_2$O; vis. UV, PMA + heat).

Analysis calc'd for $C_{25}H_{28}N_2OS \cdot HCl$: C, 68.08; H, 6.63; N, 6.35; Cl, 8.04; S, 7.27; Found: C, 68.21; H, 6.72; N, 6.40; Cl, 7.91; S, 7.15.

EXAMPLE 5

N-[4-(Dimethylamino)butyl]-N-[2-[(phenylmethyl)thio]phenyl]benzeneacetamide oxalate (1:1) salt A. N-(4-Bromobutyl)-N-[2-[(phenylmethyl)thio]phenyl]benzeneacetamide The title A compound from Example 3 above, (7.1 g, 0.021 mol) was reacted in 120 ml of toluene with 1.1 g (0.023 mol) of 50% sodium hydride. This solution was thereafter cooled to 25° C., treated with 7.5 ml (0.063 mol) of 1,4-dibromobutane and heated to reflux for 5 hours to give 16.3 g of an oil. In order to remove as much excess dibromide as possible, as well as mineral oil from the sodium hydride, the material was stirred with 50 ml of hexane and the hexane liquor decanted. The process was repeated twice with 25 ml of hexane and remaining solvent was removed on a rotary evaporator to give 9.3 g of a mixture of the title A compound and the bis derivative as a yellow oil.

B. N-[4-(Dimethylamino)butyl]-N-[2-[(phenylmethyl)thio]phenyl]benzeneacetamide oxalate (1:1) salt The title A mixture prepared above (9.1 g) was dissolved in 130 ml of methanol, stirred, and treated with 25 ml of 40% aqueous dimethylamine; a small amount of heavy yellow oil separated. After stirring for 6 hours at room temperature, the mixture was allowed to stand for 2 days.

The supernatant liquor was decanted from the undissolved fraction, the solid was filtered off, washed with methanol, and air-dried. The filtrate was concentrated on a rotary evaporator to remove the bulk of methanol and excess dimethylammonia and the residue was shaken with 100 ml of ether and a solution of 3 ml of concentrated hydrochloric acid in 50 ml of water. The hydrogen chloride salt of the product separated as a heavy oil which was separated with the aqueous phase. The ether layer was extracted with 30 ml of water and the combined aqueous layers were layered over with 50 ml of ether and basified portionwise with 6 g of potassium carbonate. After separating, the aqueous phase was extracted with ether (3×30 ml), the combined organic layers were dried over magnesium sulfate, and the solvent evaporated over magnesium sulfate to give 4.8 g of a pale yellow viscous oil.

The base (4.5 g) was dissolved in 20 ml of isopropyl alcohol and treated with a warm solution of 0.94 g of oxalic acid in 10 ml of isopropyl alcohol. The oxalate salt separated as an oil but on seeding and rubbing it slowly crystallized. Several volumes of ether were added to complete the precipitation and on continued rubbing all of the material crystallized. After cooling overnight, the colorless solid was filtered under argon, washed with ether, and dried in vacuo (4.7 g), m.p. 143°–146° (s, 137°). Following crystallization from 15 ml of MeCN, the title compound weighed 4.1 g, m.p. 148°–150° (s. 145°). TLC: $R_f$ 0.81 (7:2:1 i—PrOH—NH$_4$OH—H$_2$O; vis. UV, PMA + heat).

Analysis calc'd for $C_{27}H_{32}N_2OS \cdot C_2H_2O_4 \cdot 0.25H_2O$: C, 66.07; H, 6.60; N, 5.32; S, 6.08; Found: C, 66.14; H, 6.56; N, 5.41; S, 5.90.

EXAMPLE 6

N-[3-(Dimethylamino)propyl]-N-[2-(phenylmethoxy)phenyl]benzeneacetamide, oxalate salt (1:1)

A. 1-Nitro-2-(phenylmethoxy)benzene

A slurry of 41.7 g (0.3 mol) of o-nitrophenol in 200 ml of ethanol was added to a stirred, cooled solution of 19.8 g (0.3 mol) of 85% potassium hydroxide in 300 ml of ethanol; a voluminous yellow-orange precipitate of the potassium salt separated. After stirring at room temperature for 45 minutes, a solution of 35.7 ml (0.3 mol) of benzyl bromide in 100 ml of ethanol was added portionwise (no temperature rise) and the mixture was stirred at room temperature for 30 minutes, then gradually heated to reflux. The solid went into solution as the color lightened from red to light yellow and potassium bromide separated. After refluxing for 3 hours, the mixture was cooled and most of the ethanol removed on a rotary evaporator. The residue was shaken with 300 ml of ether and 100 ml of water and the layers separated. The aqueous phase was extracted with ether (2×100 ml) and the combined ether layers were washed with 50 ml of water and 50 ml of saturated sodium chloride solution. After drying over magnesium sulfate, the solvent was evaporated to give 66.1 g of a red-orange oil which was fractionated to yield 44.3 g of the title A compound as a yellow oily product, b.p. 163°–166° (0.2 mm). Lit. b.p. 127°–129° (0.05 mm); *J. Org. Chem.*, 37, 1848 (1972).

B. 2-Benzyloxyaniline

A solution of 20 g (0.087 mol) of the title A compound in 100 ml of ethanol (under argon) was treated with a slurry of 1 teaspoon of activated Ra/Ni in 100 ml of ethanol and shaken on the Parr hydrogenator at a starting pressure of 50 pounds. The reduction was complete in about 20 minutes, but the mixture was kept on the Parr for a total of 1 hour.

The catalyst was filtered off (under argonCelite mat), washed with ethanol, and the filtrate evaporated, finally at 0.2 mm, to give 16.7 g of a greenish oil. This was combined with 8.7 g from an earlier experiment and fractionated to yield 17.6 g of the title B compound as a light yellow-orange oil; b.p. 135°–138° (0.1–0.2 mm). The material solidified on storing in the cold. Lit. b.p. 56°–160° (0.5–1.0 mm); lit. m.p. 37°–39°; *Biochem. Pharm.*, 894 (1968).

C. N-[2-(Phenylmethoxy)phenyl]benzeneacetamide

The title B compound (7.7 g, 0.039 mol) was reacted with 5.2 ml (0.039 mol) of phenylacetyl chloride in 80 ml of chloroform in the presence of 5.5 ml (0.039 mol of triethylamine to give a solid residue which was digested with 30 ml of hot hexane and cooled to give 10.8 g of nearly colorless product; m.p. 96° C.–98° C. (s, 94°). Following crystallization from 20 ml of hot ethyl acetate-50 ml of hexane, the colorless title C material weighed 10.1 g; m.p. 98° C.–100° C. TLC: $R_f$ 0.58 (1:1 ethyl acetate-hexane; vis, UV, PMA + heat).

Analysis calc'd for $C_{21}H_{19}NO_2$: C, 79.47; H, 6.03; N, 4.41; Found: C, 79.72; H, 6.17; N, 4.42.

D. N-[3-(Dimethylamino)propyl]-N-[2-(phenylmethoxy)phenyl]benzeneacetamide, oxalate salt (1:1)

A stirred solution of the title C compound (9.75 g, 0.031 mol) in 150 ml of toluene was treated first with 1.55 g (0.032 mol) of 50 percent sodium hydride (vigorous gas evolution at 75°–85°), then with 18.2 ml (0.039 mol) of a 2.15N toluene solution of 3-dimethylaminopropyl chloride as described in part C of Example 2 above (refluxed 5 hours) to give 9.3 g of a yellow oil. Since salts such as hydrogen chloride, hydrogen bromide, maleate, and mesylate were oils or gums, the solid oxalate salt was prepared. The base in 20 ml of isopropyl alcohol was treated with a warm solution of 2.1 g of oxalic acid in 10 ml of isopropyl alcohol; the solid oxalate salt separated as a voluminous precipitate. After cooling overnight, the colorless material was filtered washed with cold isopropyl alcohol and with ether, and dried in vacuo (9.4 g); m.p. 159° C.–161° C. (s. 156°). Crystallization from 170 ml of acetonitrile provided 8.3 g of the title compound; m.p. 163° C. –165° C. TLC: $R_f$ 0.66 (7:2:1 i—PrOH—NH$_4$OH—H$_2$O; vis. UV, PMA+heat).

Analysis calc'd for $C_{26}H_{30}N_2O_2 \cdot C_2H_2O_4$: C, 68.27; H, 6.55; N, 5.80; Found: C, 68.06; H, 6.70; N, 6.03.

EXAMPLE 7

2′-(Benzylthio)-N-[3-(dimethylamino)propyl]benzanilide, hydrochloride

Using the methodology described in Example 3 but substituting benzoyl chloride for the phenylacetyl chloride in part A, the title compound is obtained. m.p. 155° C.–156° C.

Analysis calc'd for $C_{25}H_{28}N_2OS \cdot HCl$ C, 68.09; H, 6.63; N, 6.35; Cl, 8.04; S, 7.27; Found: C, 68.34; H, 6.44; N, 6.40; Cl, 8.14; S, 7.28.

EXAMPLE 8

(SQ 29,296)

N-[3-(Dimethylamino)propyl]-N-[4,5-dimethoxy-2-sulfonyl),[(phenylmethyl)thio]phenyl]benzeneacetamide, oxalate (1:1) salt A. 1-Bromo-4,5-dimethoxy-2-nitrobenzene 4-Bromoveratrole (50 g, 0.23 mol) was added dropwise at 6°–9° to a stirred solution of 175 ml of concentrated nitric acid and glacial acetic acid (525 ml). After stirring at 6°–11° for 1.5 hours, the mixture was poured into 2.5 liters of ice-water. The light yellow solid was filtered after 0.5 hour, washed with water, and air-dried (62.5 g); m.p. 120°–122° (s. 118°). Following crystallization from 400 ml of ethanol, the title A compound as a light yellow product weighed 50.0 g; m.p. 121°–123°. Lit. m.p. 120°–122°, 122°–124° (J. Org. Chem., 25, 724 (1960).

B. 1,2-Dimethoxy-4-nitro-5-[(phenylmethyl)thio]benzene

A stirred solution of 11.9 g (0.18 mol) of 85 percent potassium hydroxide in 240 ml of ethanol was cooled to 10° and treated dropwise with 21.1 ml (0.18 mol) of benzyl mercaptan dissolved in 60 ml of ethanol. After stirring at room temperature for 30 minutes, the title A compound (47.2 g, 0.18 mol) was added portionwise at <20°. The solution was stirred at room temperature for 15 minutes, then heated to reflux; the product separated as a heavy yellow precipitate. Ethanol (500 ml) was added to facilitate stirring and the mixture was refluxed for three hours. (The material did not go into solution). The mixture was cooled to 20°, diluted with 500 ml of water, and, after stirring for one hour, the bright yellow solid was filtered, washed with water, and air-dried (52.1 g), m.p. 174°–176° (s. 171°). Crystallization from 900 ml of acetonitrile yielded 50.0 g of the bright yellow title B product, m.p. 174°–176°.

Analysis calc'd for $C_{15}H_{15}NO_4S$: C, 59.00; H, 4.95; N, 4.59; S, 10.50; Found: C, 58.97; H, 4.98; N, 4.59; S, 10.44.

C. 4,5-Dimethoxy-2-[(phenylmethyl)thio]benzenamine

A slurry of 24.4 g (0.080 mol) of the title B compound in 200 ml of methanol was added to a stirred solution of 65 g (0.29 mol) of $SnCl_2 \cdot 2H_2O$ in 170 ml of concentrated hydrochloric acid; the temperature rose to 35°. On heating to reflux (45 minutes) a nearly colorless solution resulted. The latter was cooled, mixed with 500 ml of ethyl acetate, stirred, and treated portionwise at 20°–24° with a cold solution of 80 g of sodium hydroxide in 100 ml of water. Since the mixture was still acidic, 30 g more of sodium hydroxide in 75 ml of water was added. A heavy colorless slurry resulted. The mixture was transferred to a separatory funnel and the organic phase was separated. The aqueous slurry was extracted with ethyl acetate (500 ml, then 2×300 ml) and the combined organic layers were dried over magnesium sulfate. After removing the solvent on a rotary evaporator, finally at 0.2 mm, the title C compound as a pale yellow solid residue weighed 22 g; m.p. 86°–88° (s. 84°). A sample crystallized from benzene-hexane was nearly colorless, m.p. 86°–88°. TLC: $R_f$ 0.33 (1:1 ethyl acetate-hexane, vis. UV, PMA+heat).

Analysis calc'd for $C_{15}H_{17}NO_2S$: C, 65.42; H, 6.22; N, 5.09; S, 11.65; Found: C, 65.49; H, 6.26; N, 4.92; S, 11.48.

D. N-[4,5-Dimethoxy-2-[(phenylmethyl)thio]phenyl]acetamide

Interaction of the title C compound (18.2 g, 0.066 mol) and 8.9 ml (0.067 mol) of phenylacetyl chloride in 135 ml of chloroform in the presence of 9.3 ml (0.067 mol) of triethylamine according to the procedure described in part B of Example 1 gave 27.4 g of a light yellow solid. Following crystallization from 60 ml of hot ethyl acetate-200 ml of hexane, the cream-colored product weighed 23.9 g, m.p. 105°–107° (s. 103°). Recrystallization from 75 ml of isopropyl alcohol gave 22.3 g of the title D compound as a nearly colorless solid, m.p. 105°–107°. TLC: $R_f$ 0.65 (ethyl acetate; vis. UV, PMA+heat).

Analysis calc'd for $C_{23}H_{23}NO_3S$: C, 70.20; H, 5.89; N, 3.56; S, 8.15; Found: c, 70.23; H, 5.91; N, 3.51; S, 8.13.

E. N-[3-(Dimethylamino)propyl]-N-[4,5-dimethoxy2-[(phenylmethyl)thio]phenyl]benzeneacetamide, oxalate (1:1) salt The title D compound (21.3 g, 0.054 mol) was treated in 250 ml of toluene with 2.7 g (0.056 mole) of 50 percent sodium hydride, then with 32 ml (0.069 mol) of a 2.15 N toluene solution of 3-dimethylaminopropyl chloride as described in part C of Example 2 above to give 23.5 g of crude base as a light yellow oil. The base (22.7 g) in 25 ml of methanol was stirred, treated with 6.1 g of barbituric acid, heated to obtain a solution, filtered to clarify, and concentrated on a rotary evaporator to approximately 50 ml. On diluting with 600 ml of ether, the solid barbiturate salt was precipitated. After cooling overnight, the nearly colorless solid was filtered, washed with ether, and dried in vacuo (25.7 g), m.p. 167°–170° (s. 160°). Following trituration with 100 ml of ethanol and cooling, the colorless solid weighed 23.9 g, m.p. 170°–173° (s. 162°). TLC: Product at $R_f$ 0.78, barbituric acid at $R_f$ 0.54 (7:2:1 i—PrOH—NH$_4$OH—H$_2$O; vis. UV, PMA — heat).

Analysis calc'd for $C_{28}H_{34}N_2O_3S \cdot C_4H_4N_2O_3 \cdot 0.5\text{-}H_2O$:

C, 62.42; H, 6.38; N, 9.10; S, 5.21; Found: C, 62.28; H, 6.35; N, 9.75; S, 4.87.

The barbiturate salt (23.7 g) was converted to 18.2 g of oily base (N NaOH; ether extractions). TLC: $R_f$ 0.80 (7:2:1 i—PrOH—NH$_4$OH—H$_2$O; vis. UV, PMA + heat).

Analysis calc'd for $C_{28}H_{34}N_2O_3S$: C, 70.26; H, 7.16; N, 5.85; S, 6.70; Found: C, 70.22; H, 7.49; N, 6.01; S, 6.49.

At this point it was found that a solid oxalate salt could be obtained.

The base (17.5 g) in 100 ml of isopropyl alcohol was treated with a warm solution of 3.3 g of oxalic acid in 50 ml of isopropyl alcohol to precipitate the oxalate salt as an oil. A solution was obtained on warming but on cooling the salt again separated as an oil. However, on seeding and rubbing the material slowly solidified. After cooling overnight, the somewhat tacky material was filtered under argon, washed with isopropyl alcohol and with ether, and dried in vacuo (18.0 g). Following crystallization from 80 ml of warm methanol −240 ml of ether (solid separated slowly), the title compound as a colorless product weighed 13.4 g, m.p. 130°-132° (bubbles), s. 125°. TLC: $R_f$ 0.78 (7:2:1 i—PrOH—NH$_4$OH—H$_2$O; vis. UV, PMA — heat).

Analysis calc'd for $C_{28}H_{34}N_2O_3S \cdot C_2H_2O_4$: C, 63.36; H, 6.38; N, 4.93; S, 5.64; Found: C, 63.40; H, 6.44; N, 4.96; S, 5.59.

EXAMPLE 9

N-[3-(Dimethylamino)propyl]-N-[4-chloro-2-[[(4-methoxyphenyl)methyl]thio]phenyl]benzeneacetamide, monohydrochloride A. 6-Chloro-1,2,3-benzodithiazol-1-ium chloride A solution of 77.0 g (0.6 mol) of p-chloroaniline in 72 ml of acetic acid was added dropwise over a period of 10 minutes to 300 ml of sulfur chloride (stirred) while maintaining the temperature at 25°-35° (evolved gas was passed over water). The mixture was then heated at 55°-65° for 3 hours and the mixture then diluted with 700 ml of benzene. After standing overnight at room temperature, the pale green solid was filtered and washed with benzene. The solid was suspended in 500 ml of benzene, stirred and filtered to give 127.7 g of pale green solid. The above material was suspended in 1.6 l of water, stirred and added 700 ml of ether. The mixture was separated and the aqueous phase was extracted with 700 ml of ether (2x). The ether phases were combined, washed with 200 ml of water, dried over magnesium sulfate, filtered and the solvent evaporated to give 104.8 g of the title A compound as a light purple solid, m.p. 105°-107°.

B. 2-Amino-5-chlorobenzenethiol, monohydrochloride

To a stirred solution of 50 g (1.25 mol) of sodium hydroxide in 500 ml of distilled water, cooled to 10° and maintained at 10°-15°, was added dropwise a solution of 50.0 g (0.22 mol) of the title A compound in 500 ml of methanol (over 20 minutes). The mixture was then stirred at room temperature for 2 hours, cooled to 20° and then neutralized to pH 6.5 with a solution of 50 ml of acetic acid in 50 ml of water. This mixture was extracted with 250 ml of ether (4x). The ether phases were combined, extracted with 100 ml of water, 100 ml of saturated sodium chloride solution (2x), dried over magnesium sulfate, filtered and the filtrate was treated with 30 ml of 6N hydrochloric acid to give the hydrogen chloride salt. The nearly colorless solid was filtered, washed with ether and dried to provide 27.2 g of the title B compound, m.p. 212° C.-214° C. (dec.). Lit. m.p. 210°-212° (*J. Med. Chem.*, 14, 248 (1971)).

Analysis calc'd for $C_6H_6ClNS \cdot HCl$: C, 36.75; H, 3.60; N, 7.14; Cl, 36.16; S, 16.35; Found: C, 36.76; H, 3.55; N, 7.10; Cl, 36.07; S, 16.15.

C. 4-Chloro-2-[[(4-methoxyphenyl)methyl]thio]benzenamine

To a stirred solution of 18.5 g (0.28 mol) of potassium hydroxide (85%) in 300 ml of ethanol (under nitrogen gas), cooled to 5°, was added portionwise 27.1 g (0.14 mol) of the title B compound over a period of 10 minutes. The cooling bath was removed, stirred at room temperature for 1 hour, cooled to 5° and added dropwise a solution of 24.0 g (0.15 mol) of 4-methoxybenzyl chloride in 40 ml of ethanol over a period of 10 minutes. The pale brown mixture was stirred at room temperature for 1 hour, and then refluxed for 3 hours, and allowed to stand overnight at room temperature. The mixture was filtered and the solid was filtered and washed with ethanol. The filtrate was concentrated on a rotary evaporator to give about 27 g of blue-green solid. This material was combined with the previous solid, dissolved in 300 ml of ethyl acetate and treated with 150 ml of water. The mixture was shaken, and the layers separated. The aqueous phase was extracted with 100 ml of ethyl acetate. The organic phases were combined, extracted with 50 ml of water (2x), and 50 ml of brine, dried over magnesium sulfate, filtered and the solvent evaporated to give 41 g of deep blue solid, m.p. 65°-70°. This material was rapidly distilled at 80°-200° at 0.1 mm as a pale yellow distillate (the blue-colored residue was discarded). The distillate was fractioned to give 3.4 g of forerun and 31.5 g of the title C compound as a colorless distillate, b.p. 170°-180° (0.05 mm), m.p. 78°-81° (s. 70°).

Analysis calc'd for $C_{14}H_{14}NClOS$: C, 60.10; H, 5.06; N, 5.01; Cl, 12.67; S, 11.46; Found: C, 60.10; H, 5.07; N, 5.05; Cl, 12.47; S, 11.49.

A sample of this material was crystallized from ethyl acetate to give a colorless crystalline material, m.p. 81°-83° (s. 78°).

D. N-[4-Chloro-2-[[(4-methoxyphenyl)methyl]thio]phenyl]benzeneacetamide

Interaction of the title C compound (30.0 g, 0.107 mol) and phenylacetyl chloride (14.5 ml, 0.11 mol) in 150 ml of chloroform in the presence of triethylamine (15.0 ml, 0.108 mol) using the procedure described in part B of Example 1 gave a solid which was digested with 100 ml of boiling hexane and allowed to cool, finally in the cold room, to yield 42.2 g of colorless material; m.p. 113°-116°, s. 105°. Following crystallization from 80 ml of acetonitrile, the title D compound weighed 32.5 g, m.p. 116°-118° (s. 111°). TLC: $R_f$ 0.50 (1:1 ethyl acetate-hexane).

Analysis calc'd for $C_{22}H_{20}ClNO_2S$: C, 66.40; H, 5.07; N, 3.52; Cl, 8.06; S, 8.91; Found: C, 66.45; H, 4.99; N, 3.57; Cl, 7.79; S, 8.66.

E. N-[3-(Dimethylamino)propyl]-N-[4-chloro-2-[[(4-methoxyphenyl)methyl]thio]phenyl]-benzeneacetamide, monohydrochloride The title D compound (15.0 g, 0.038 mol) in 190 ml of toluene was treated with 2.0 g (0.042 mol) of 50% sodium hydride, then with 25 ml of a 2.15 N toluene solution of 3-dimethylaminopropyl chloride as described in part C of Example 1 above to give 19.4 g of syrupy base which solidified on standing. Crystallization (of 19.0 g) from 60 ml of isopropyl alcohol yielded 12.8 g of colorless solid; m.p. 56°–58°. TLC: $R_f$ 0.36 (8:1:1 (methylene chloride-methanol-acetic acid).

Analysis calc'd for $C_{27}H_{31}ClN_2O_2S.0.5\ C_3H_7OH$: C, 66.71; H, 6.88; N, 5.46; Cl, 6.91; S, 6.25 Found: C, 66.23; H, 6.89; N, 5.45; Cl, 7.01; S, 6.27.

A solution of the base (12.6 g) in 350 ml of ether was treated with 4.7 ml of 5.75 N ethanolic hydrochloric acid to precipitate the hydrogen chloride salt as a viscous oil. A sample of the latter solidified when rubbed under ether in the presence of a trace of water. All of the mixture was treated with 4 ml of water and rubbed; the hydrogen chloride salt readily solidified. After allowing to crystallize at room temperature with occasional rubbing, then cooling overnight, the colorless hydrogen chloride salt was filtered, washed with ether, and dried in vacuo (13.7 g), m.p. 100°–102° (bubbles), s. 96°. Following crystallization from 50 ml of hot 95% ethanol − 300 ml of ether, the title compound weighed 13.25 g, m.p. 110°–112° (bubbles), s. 108°. TLC: $R_f$ 0.33 (8:1:1 methylene chloride-methanol-acetic acid).

Analysis calc'd for $C_{27}H_{31}ClN_2O_2S.HCl\ H_2O$: C, 60.32; H, 6.38; N, 5.21; Cl, 13.19; S, 5.97 Found: C, 60.04; H, 6.67; N, 5.07; Cl, 12.91; S, 5.69.

EXAMPLES 10–31

Utilizing the procedures described above and in Examples 1–9, the following compounds were also prepared.

EXAMPLE 10

N-[2-(Dimethylamino)ethyl]-N-[2-[[(4-methoxyphenyl)methyl]thio]phenyl]-3-phenyl-2-propenamide, monohydrochloride Utilizing the procedure of Example 2 but substituting an equivalent quantity of cinnamoyl chloride for the phenylacetyl chloride in part B and replacing the 3-dimethylaminopropyl chloride by 2-dimethylaminoethyl chloride in part C, the title compound was crystallized from methyl alcohol-ether, m.p. 220°–222° (dec.).

Analysis calc'd for $C_{27}H_{30}N_2O_2S.HCl$: C, 67.13; H, 6.47; N, 5.80; Cl, 7.34; S, 6.64; Found: C, 66.95; H, 6.60; N, 5.75; Cl, 7.32; S, 6.63.

EXAMPLE 11

N-[2-(Dimethylamino)ethyl]-3-phenyl-N-[2-[(phenylmethyl)thio]phenyl]-2-propenamide, monohydrochloride Utilizing the procedure of Example 3 but substituting an equivalent quantity of cinnamoyl chloride for the phenylacetyl chloride in part B and replacing the 3-dimethylaminopropyl chloride by 2-dimethylaminoethyl chloride in part C, the title compound was crystallized from isopropanol, m.p. 188°–190°.

Analysis calc'd for $C_{26}H_{28}N_2OS.HCl$: 6B.93; H, 6.45; N, 6.18; Cl, 7.83; S, 7.08; Found: C, 68.94; H, 6.57; N, 6.15; Cl, 7.70; S, 7.01.

EXAMPLE 12

2'-(Benzylthio)-4-chloro-N-[3-(dimethylamino)propyl]-benzanilide, hydrochloride

Utilizing the procedure of Example 3 but substituting p-chlorobenzoyl chloride for the phenylacetyl chloride in part A, the title compound melted at 197°–199°.

Analysis calc'd for $C_{25}H_{27}ClN_2OS.HCl$: C, 63.15; H, 5.94; N, 5.89; Cl, 14.91; S, 6.75; Found: C, 63.34; H, 5.82; N, 5.89; Cl, 15.11; S, 6.64.

EXAMPLE 13

2'-(Benzylthio)-N-[3-(dimethylamino)propyl]isonicotinanilide, hydrochloride, hydrate (1:2:1)

Utilizing the procedure of Example 3 but substituting isonicotinoyl chloride for the phenylacetyl chloride in part A, the title compound melted at 230°–232°.

Analysis calc'd for $C_{24}H_{27}N_3OS.2HCl.H_2O$: C, 58.05; H, 6.29; N, 8.47; Cl, 14.28; S, 6.46; Found: C, 58.33; H, 6.44; N, 8.59; Cl, 14.26; S, 6.44.

EXAMPLE 14

N-[2-(Dimethylamino)ethyl]-N-[2-[(phenylmethyl)thio]-4-(trifluoromethyl)phenyl-2-propenamide, monohydrochloride Utilizing the procedure of Example 8 but substituting 4-chloro-3-nitrobenzotrifluoride for the 4-bromoveratrole in part A, replacing the phenylacetyl chloride by cinnamoyl chloride in part D and using 2-dimethylaminoethyl chloride in place of 3-dimethylaminopropyl chloride in part E gave the title compound which was crystallized from ethanol-ether, m.p. 187°–189°.

Analysis calc'd for $C_{27}H_{27}F_3N_2OS\ HCl$: C, 62.24; H, 5.42; N, 5.38; F, 10.94; Cl, 6.81; S, 6.15; Found: C, 62.35; H, 5.46; N, 5.26; F, 10.8; Cl, 6.77; S, 6.17.

EXAMPLE 15

N-[2-(Dimethylamino)ethyl]-3-phenyl-N-[2-[(2-(phenylethyl)thio]phenyl]-2-propenamide, monohydrochloride Utilizing the procedure of Example 1 but substituting phenethyl bromide for 4-chlorobenzyl chloride in part A, cinnamoyl chloride for phenylacetyl chloride in part B and 2-dimethylaminoethyl chloride for 3-dimethylaminopropyl chloride in part C. After the title compound was crystallized from isopropanol, it was triturated with cold water and dried; m.p. 197°–199°.

Analysis calc'd for $C_{27}H_{30}N_2OS.HCl$: C, 69.43; H, 6.69; N, 6.00; Cl, 7.59; S, 6.86; Found: C, 69.64; H, 6.73; N, 6.07; Cl, 7.62; S, 7.12.

EXAMPLE 16

N-[2-(Dimethylamino)ethyl]-3-phenyl-N-[2-(phenylmethoxy)phenyl]-2-propenamide, monohydrochloride Utilizing the procedure of Example 6 but substituting cinnamoyl chloride for phenylacetyl chloride in part C, 2-dimethylaminoethyl chloride for 3-dimethylaminopropyl chloride in part D, and hydrogen chloride in place of oxalic acid in part D, the title compound was crystallized from isopropanol, m.p. 195°–197°.

Analysis calc'd for $C_{26}H_{28}N_2O_2.HCl$: C, 71.46; H, 6.69; N, 6.41; Cl: 8.11; Found: C, 71.10; H, 6.66; N, 6.50; Cl, 7.77.

EXAMPLE 17

N-[2-(Dimethylamino)ethyl]-3-phenyl-N-[2-[(1-phenylethyl)thio]phenyl-2-propenamide, monohydrobromide Following the procedure described in Example 1 but substituting 1-bromoethylbenzene for 4-chlorobenzyl chloride in part A, cinnamoyl chloride in place of phenylacetyl chloride in part B, 2-dimethylaminoethyl chloride for 3-dimethylaminopropyl chloride in part C and used hydrogen bromide to prepare a salt of the title compound. After crystallization from isopropanol, the colorless product melted at 146°–148°.

Analysis calc'd for $C_{27}H_{30}N_2OS \cdot HBr$: C, 63.40; H, 6.11; N, 5.48; Br, 15.62; S, 6.27; Found: C, 63.19; H, 6.22; N, 5.41; Br, 15.70; S, 6.05.

EXAMPLE 18

N-[2-(Dimethylamino)ethyl]-N-[2-[(phenylmethyl)thio]phenyl]benzamide, monohydrochloride Following the procedure described in Example 3 but substituting benzoyl chloride for phenylacetyl chloride in part A and 2-dimethylaminoethyl chloride for 3-dimethylaminopropyl chloride in part B, the title compound is obtained. After crystallization from isopropanol, the colorless solid melted at 177°–179°.

Analysis calc'd for $C_{24}H_{26}N_2OS \cdot HCl$: C, 67.50; H, 6.37; N, 6.56; Cl, 8.30; S, 7.51; Found: C, 67.26; H, 6.47; N, 6.45; Cl, 8.02; S, 7.29.

EXAMPLE 19

N-[2-(Dimethylamino)ethyl]-α-oxo-N-[2-[(phenylmethyl)thio]phenyl]benzeneacetamide, monohydrochloride Utilizing the method described in Example 3 but substituting benzoylformic acid and dicyclohexylcarbodiimide for the phenylacetyl chloride in part A and 2-dimethylaminoethyl chloride in place of 3-dimethylaminopropyl chloride in part B, the title compound is obtained. After crystallization from acetonitrile, the material melted at 178°–180°.

Analysis calc'd for $C_{25}H_{26}N_2O_2S \cdot HCl$: C, 65.99; H, 5.98; N, 6.16; Cl, 7.79; S, 7.05; Found: C, 66.14; H, 6.16; N, 6.27; Cl, 7.77; S, 6.78.

EXAMPLE 20

N-[2-(Dimethylamino)ethyl]-α-hydroxy-N-[2-[(phenylmethyl)thio]phenyl]benzeneacetamide, monohydrochloride A solution of Example 19 in methanol was treated with sodium borohydride at room temperature in the usual manner. This product was converted to the hydrochloride salt and crystallized from methanol-ether, m.p. 213°–215° (dec.).

Analysis calc'd for $C_{25}H_{28}N_2O_2S \cdot HCl$: C, 65.70; H, 6.40; N, 6.13; Cl, 7.76; S, 7.02; Found: C, 65.73; H, 6.64; N, 6.03; Cl, 7.61; S, 6.79.

EXAMPLE 21

N-[3-(Dimethylamino)propyl]-N-[2-[(phenylmethyl)thio]phenyl]benzenepropanamide, monohydrobromide Following the procedure of Example 3 but substituting hydrocinnamoyl chloride for phenylacetyl chloride in part A and using hydrogen bromide in place of hydrogen chloride in part B, the title compound is obtained. After recrystallization from isopropyl alcohol, the product melted at 139°–141°.

Analysis calc'd for $C_{27}H_{32}N_2OS \cdot HBr$: C, 63.14; H, 6.48; N, 5.46; Br, 15.56; S, 6.24; Found: C, 63.08; H, 6.51; N, 5.47; Br, 15.62; S, 5.95.

EXAMPLE 22

N-3-(Dimethylamino)propyl]-N-[2-[(phenylmethyl)thio]phenyl]hexanamide, monohydrochloride A. 2-(Benzylthio)-N-[3-(dimethylamino)propyl]aniline A stirred solution of 21.5 g (0.10 mol) of 2-(benzylthio)aniline in 500 ml of toluene was treated with 5.0 g (0.104 mol) of 50 percent sodium hydride (oil dispersion) and gradually heated. After a few minutes at reflux, the mixture began to darken and the sodium salt separated. After stirring and refluxing for 1 hour, the dark mixture was cooled to 25°, treated with 59 ml (0.127 mol) of a 2.15N toluene solution of 3-dimethylaminopropyl chloride, refluxed for 5 hours, and kept overnight at room temperature.

The mixture was shaken with 100 ml of water, then extracted with a cold solution of 20 ml of concentrated hydrochloric acid in 250 ml of water, followed by 100 ml of water. The combined aqueous extracts were washed with 100 ml of ether, layered over with 250 ml of ether, and basified protionwise with 40 g of potassium carbonate. The layers were separated and the aqueous phase was extracted with ether (3×100 ml).

After drying the combined organic layers over magnesium sulfate, the solvent was evaporated, finally at 0.2 mm, to give 24.3 g of a red-brown oil. The latter was distilled and material boiling at 172°–177° (0.1–0.2 mm) was fractionated to yield 18.5 g of the title A compounds as a yellow oil; b.p. 174°–177°. (0.1–0.2 mm).

Analysis calc'd for $C_{18}H_{24}N_2S$: C, 71.95; H, 8.05; N, 9.32; S, 10.67; Found: C, 71.83; H, 8.21; N, 9.35; S, 10.54.

B. N-[3-(Dimethylamino)propyl]-N-[2-[(phenylmethyl)thio]phenyl]hexanamide, monohydrochloride A solution of 17.9 g (0.06 mol) of the title A compound and 8.3 ml (0.06 mol) of triethylamine in 30 ml of chloroform was added dropwise at 12°–17° to a stirred solution of 8.4 ml (0.06 mol) of hexanoyl chloride in 90 ml of chloroform. After the addition, the solution was stirred at room temperature for 1 hour, refluxed for 1 hour, and kept overnight at room temperature.

The solution was stirred with a cold solution of 8.2 g of potassium carbonate in 60 ml of water and the layers separated (added some saturated sodium chloride and methanol to break up emulsion). The aqueous phase was extracted with chloroform (2×30 ml), the combined organic layers washed with 30 ml of saturated sodium chloride, dried over anhydrous magnesium sulfate, and the solvent evaporated to give 26.3 g of a yellow oil. Since a sample in ether left some solid undissolved, all of the material was shaken with 300 ml of ether and 50 ml of water and the layers separated. The ether layer was washed with water (2×25 ml), dried, and evaporated to give 23.0 g of a yellow oil.

The base (22.7 g) in 300 ml of ether was treated with 10.8 ml of 5.3N ethanolic hydrochloric acid to precipitate the hydrogen chloride salt as an oil which readily crystallized on seeding and rubbing. After cooling overnight, the colorless solid was filtered under argon, washed with ether, and dried in vacuo, (22.0 g), m.p. 115°–118° (s. 80°). Crystallization from 45 ml of butanone gave 15.8 g; m.p. 123°–126° (s. 85°). The IR spectrum indicated a hydrate. Following recrystallization from 45 ml of warm acetonitrile-200 ml of ether, the colorless title product weighed 13.7 g; m.p. 127°–130° (bubbles).

Analysis calc'd for $C_{24}H_{34}N_2OS.HCl\ 0.75\ H_2O$: C, 64.26; H, 8.20; N, 6.25; Cl, 7.90; S, 7.05; Found: C, 64.36; H, 7.94; N, 6.39; Cl, 7.84; S, 6.77.

EXAMPLE 23

N-3-(Dimethylamino)propyl]-3-phenyl-N-[2-[(phenylmethyl)thiophenyl]-2-propynamide, oxalate salt (1:1)

Utilizing the procedure described in Example 3 but substituting phenylpropioloyl chloride for phenylacetyl chloride in part A, the title compound was obtained. This oxalate salt was crystallized from acetonitrile, m.p. 154°–156°.

Analysis calc'd for $C_{27}H_{28}N_2OS.C_2H_2O_4$: C, 66.5g; H, 5.88; N, 5.36; S, 6.13; Found: C, 66.74; H, 5.98; N, 5.40; S, 6.12.

EXAMPLE 24

N-[4-(Dimethylamino)butyl]-3-phenyl-N-[2-[(phenylmethyl)thio]phenyl]-2-propenamide, oxalate salt (1:1)

Following the method described in Example 5 but substituting the product of the reaction of 2-(benzylthio)aniline and cinnamoyl chloride for the 2-(benzylthio)phenylacetanilide in part A, the title compound is obtained. After crystallization from acetonitrile, the colorless solid melted at 137°–139°.

Analysis calc'd for $C_{28}H_{32}N_2OS\ C_2H_2O_4$: C, 66.27; H, 6.49; N, 5.15; S, 5.90; Found: C, 66.29; H, 6.41; N, 5.28; S, 5.65.

EXAMPLE 25

N-[3-(Dimethylamino)propyl]-4-methoxy-N-[2-[(phenylmethyl)thio]phenyl]benzeneacetamide acid, monohydrochloride Following the procedure described in Example 22 but substituting 4-methoxyphenylacetyl chloride for the hexanoyl chloride in part B, the title compound is obtained. After crystallization from 95 percent alcohol-ether, the colorless solid melted at 74°–76°.

Analysis calc'd for $C_{27}H_{32}N_2O_2S.HCl.H_2O$: C, 64.45; H, 7.01; N, 5.57; Cl, 7.05; S, 6.37; Found: C, 64.63; H, 6.78; N, 5.63; Cl, 7.25; S, 6.07.

EXAMPLE 26

N-[5-(Dimethylamino)pentyl]-3-phenyl-N-[2-[(phenylmethyl)thio]phenyl]-2-propenamide Following the method described in Example 5 but substituting the product of the reaction of 2-(benzylthio)aniline and cinnamoyl chloride for the 2-(benzylthio)phenylacetanilide and using 1,5-dibromopentane in place of 1,4-dibromobutane, the title compound is obtained. This material was isolated as a pale yellow oil.

Analysis Calc'd for $C_{29}H_{34}N_2OS$: C, 75.g4; H, 7.47; N, 6.11; S, 6.99; Found: C, 76.06; H, 7.54; N, 6.08; S, 6.79.

EXAMPLE 27

N-[3-(Dimethylamino)propyl]-N-[2-[(phenylmethyl)thio]phenyl]cyclohexaneacetamide monohydrochloride Following the procedure described in Example 22 but substituting cyclohexylacetyl chloride for the hexanoyl chloride in part B, the title compound is obtained. After crystallization from methanol-ether and trituration with cold water, the colorless product melted at 157°–159°.

Analysis calc'd for $C_{26}H_{36}N_2OS.HCl.H_2O$: C, 65.17; H, 8.20; N, 5.85; Cl, 7.40 S, 6.69; Found: C, 64.87; H, 7.97; N, 5.83; Cl, 7.44; S, 6.58.

EXAMPLE 28

α-(Acetyloxy)-N-[3-(dimethylamino)propyl]-N-[2-[(phenylmethyl)thio]phenyl]benzeneacetamide, monohydrochloride Utilizing the procedure described in Example 22 but substituting o-acetylmandelic acid chloride for the hexanoyl chloride in part B, the title compound is obtained. After crystallization from methanol-ether, the colorless solid melted at 180°–182°.

Analysis calc'd for $C_{28}H_{32}N_2O_3S.HCl.0.25H_2O$: C, 64.g7; H, 6.52; N, 5.41; Cl, 6.85; S, 6.20; Found: C, 65.15; H, 6.40; N, 5.53; Cl, 6.94; S, 6.03.

EXAMPLE 29

N-[3-(Dimethylamino)propyl]-3-phenyl-N-[2-(phenylmethoxy)phenyl]-2-propenamide, monohydrochloride Following the method described in Example 5 but substituting cinnamoyl chloride for the phenylacetyl chloride in part C, the title compound is obtained. After crystallization from methanol-ether, the colorless solid melted at 182°–184°.

Analysis calc'd for $C_{27}H_{30}N_2O_2HCl$: C, 71.90; H, 6.93; N, 6.21; Cl, 7.86 Found: C, 71.90; H, 7.02; N, 7.14; Cl, 7.74.

EXAMPLE 30

N-[3-(Dimethylamino)propyl]-N-[2-[(phenylmethyl)thio]phenyl]benzeneacetamide, monohydrobromide Utilizing the procedure described in Example 3 but substituting 2-(phenylthio)aniline (*J. Pharm. Sci.*, 57, 979 (1968) for the 2-benzylthio)aniline in part A, the title compound is obtained. This material was crystallized from isopropanol-ether, suspended in cold water and filtered to give a colorless solid, m.p. 172°–174°.

Analysis calc'd for $C_{25}H_{28}N_2OS.HBr$: C, 61.85; H, 6.02; N, 5.77; Br, 16.46; S, 6.60; Found: C, 61.86; H, 6.00; N, 6.04; Br, 16.67; S, 6.34.

EXAMPLE 31

4-Chloro-N-[3-(Dimethylamino)propyl]-N-[2-[(phenylmethyl)thio]phenyl]benzeneacetamide, monohydrochloride Utilizing the procedure described in Example 22 but substituting 4-chlorophenylacetyl chloride for the hexanoyl chloride in part B, the title compound is obtained. After crystallization from isopropanol-ether and suspending in cold water, the colorless solid melted at 65°–68°.

Analysis calc'd for $C_{26}H_{29}ClN_2OS.HCl.2\ H_2O$: C, 59.42; H, 6.52; N, 5.33; Cl, 13.49; S, 6.10; Found: C, 59.84; H, 6.64; N, 5.35; Cl, 13.69; S, 5.95.

EXAMPLE 32

N-3-(Dimethylamino)propyl]-N-[2-[(phenylmethyl)thio]phenyl]benzenemethanesulfonamide, monohydrochloride Utilizing the procedure described in Example 3 but substituting benzylsulfonyl chloride for phenylacetyl chloride in part A, the title compound was obtained.

After crystallization from acetonitrile, the colorless solid melted at 137°–139°.

Analysis calc'd for $C_{25}H_{30}N_2O_2S_2 \cdot HCl \cdot 0.25\ H_2O$: C, 60.54; H, 6.40; N, 5.65; Cl, 7.15; S, 12.93; Found: C, 60.68; H, 6.40; N, 5.32; Cl, 7.03; S, 12.97.

EXAMPLE 33

Preparation of the Isolated Perfused Hearts

Male Sprague-Dawley rats (450–550 g) were used in all experiments. The rats were anesthetized using 30 mg/kg sodium pentobarbital (i.p.). They were intubated and then treated with i.v. heparin (1000 U/kg). While being mechanically ventilated, their hearts were perfused in situ via retrograde cannulation of the aorta. The hearts were then excised and quickly moved to a Langendorff apparatus where they were perfused with Krebs-Henseleit bicarbonate buffer (112 mM NaCl, 5 mM KCl, 1.2 mMMg $SO_4$, 1 mM $KH_2PO_4$, 1.25 mM $CaCl_2$, 11.5 mM dextrose, and 2 mM pyruvate) at a constant pressure (75 mm Hg). A water filled latex balloon attached to a metal cannula was then inserted into the left ventricle and connected to a Statham pressure transducer for measurement of left ventricular pressure. The hearts were allowed to equilibrate for 15 minutes at which time end diastolic pressure (EDP) was adjusted to 5 mm Hg and this was maintained for 5 minutes. Pre-ischemia or pre-drug function, heart rate and coronary blood flow (extracorporeal electromagnetic flow probe, Carolina Medical Electronics, King, N.C.) were then measured. Cardiac function was determined using the double product of heart rate (HR) times left ventricular developed pressure (LVDP) divided by 1,000.

Once the baseline measurements were taken, the hearts were treated with 1.0 μM of one of compounds 1–9 or diltiazem (n = 4–6 per group) or with vehicle buffer (n = 6). All of these hearts were treated with their respective drugs or vehicle for ten minutes. At this time, post-drug cardiac function and flow were measured and then the hearts were made globally ischemic by shutting off the buffer perfusion. The ischemia was maintained for 25 minutes at which time reperfusion with nondrug treated buffer was instituted. Reperfusion was maintained for 30 minutes and at this time reperfusion function and flow were again determined.

Determination of LDH Release

At the end of the reperfusion period, the reperfusion buffer was sampled for cumulative LDH release as previously described. LDH release was expressed as U/g preischemia heart weight for the 30 minute collection period. LDH release is a sensitive index for loss of cell viability. Determination of the relationship between pre-ischemic, post-drug cardiac function was made by dividing the double product (HR × LVDP/1000) by the cumulative LDH release.

All data were analyzed using a one way analysis of variance. Multiple comparisons were done using the Duncan procedure. All data are expressed as the mean ± SE. Cardiac functional and flow changes for vehicle and drug treated hearts before and after ischemia are shown in Table 1.

The pre-ischemia DP values are a measure of the cardiodepression of the drug on the healthy cardiac tissue. The drugs having the lower DP values are more cardiodepressant than those having the higher DP values. Each of compounds 1–9 were found to be less cardiodepressant than diltiazem by this test.

The post-ischemia LDH values are a measure of the cardioprotection or anti-ischemic activity of the drug. In this case, lower values indicate greater anti-ischemic activity or greater cardioprotection. Compounds 1, 2 and 9 were found to be comparable to diltiazem in cardioprotection and compounds 3 and 6–8 offered more cardioprotection than diltiazem.

The LDH/DP values are the ratio of cardioprotection to cardiodepression, the lower values indicating a greater selectivity for anti-ischemic activity. All of compounds 1–9 had a greater selectivity of anti-ischemic activity compared to diltiazem.

The post-ischemia DP indicates cardiodepression after the ischemic episode and the lower DP values here are indicative of agents which still remained in the cardiac tissue for more than 30 minutes post ischemia.

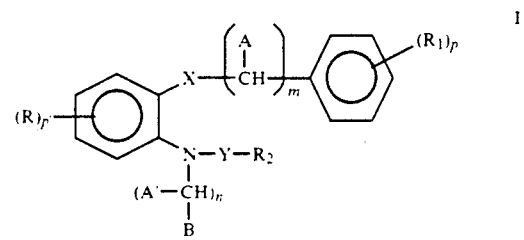

TABLE 1

Effect of Substituted Anilides and Sulfonamides on the Ischemic and Nonischemic Isolated Rat Heart

| Compound | Preischemia (Post Drug) | | | | Postischemia (30 min.) | | | | | |
|---|---|---|---|---|---|---|---|---|---|---|
| | HR | LVDP | DP | FLOW | HR | LVDP | DP | FLOW | LDH | LDH/DP |
| Vehicle | 244 | 134 | 33 | 13 | 215 | 30 | 7 | 10 | 20 | 0.62 |
| Diltiazem | 217 | 45 | 10 | 22 | 231 | 104 | 24 | 17 | 10 | 0.98 |
| Ex. 1 | 229 | 90 | 21 | 25 | 211 | 34 | 7 | 12 | 12 | 0.55 |
| Ex. 2 | 219 | 135 | 29 | 20 | 188 | 73 | 14 | 11 | 8.9 | 0.30 |
| Ex. 3 | 243 | 79 | 19 | 18 | 238 | 93 | 22 | 11 | 5.2 | 0.30 |
| Ex. 4 | 236 | 123 | 30 | 20 | 239 | 60 | 15 | 15 | 21 | 0.79 |
| Ex. 5 | 253 | 115 | 29 | 15 | 180 | 51 | 10 | 11 | 16.5 | 0.57 |
| Ex. 6 | 230 | 113 | 26 | 15 | 222 | 89 | 20 | 10 | 5.7 | 0.22 |
| Ex. 7 | 218 | 132 | 29 | 11 | 220 | 72 | 15 | 8 | 6.7 | 0.24 |
| Ex. 8 | 216 | 65 | 14 | 19 | 246 | 71 | 17 | 8 | 3.7 | 0.26 |

TABLE 1-continued

Effect of Substituted Anilides and Sulfonamides on the
Ischemic and Nonischemic Isolated Rat Heart

| Compound | Preischemia (Post Drug) | | | | Postischemia (30 min.) | | | | | |
|---|---|---|---|---|---|---|---|---|---|---|
| | HR | LVDP | DP | FLOW | HR | LVDP | DP | FLOW | LDH | LDH DP |
| Ex. 9 | 226 | 126 | 29 | 18 | 214 | 52 | 11 | 9 | 8.2 | 0.29 |

Concentration 1 μM
Occlusion 25 minutes
Reperfusion 30 minutes
HR = Heart Rate (beats/min)
LVDP = Left Ventricular Developed Pressure (mmHg)
DP = Double Product
LDH = Lactate Dehydrogenase Release

EXAMPLE 34

The calcium channel blocking and sodium entry blocking activities of compounds of the present invention were tested using standard microelectrode techniques in isolated canine cardiac Purkinje fibers as reported in J. L. Bergey et al., "Antiarrhythmic, hemodynamic, and cardiac electrophysiological evaluation of N-(2,6-dimethylphenyl)-N'-[3-(1-methylethylamino)-propyl]-urea), (Wy 42,362)", Arzneim.-Forsch. 33:1258, 1983). Table 2 shows the effects of compounds of the present invention on the calcium-dependent slow response action potential (SAPA). Depression of this parameter indicates depression of calcium entry into cardiac tissue. Similarly, Table 3 shows effects of the compounds on normal action potential parameters. Significant depression of the upstroke velocity (vmax) indicates the blocking of sodium entry into cardiac tissue.

TABLE 2

IC$_{50}$ values for compounds of Examples 1, 3 and 24 in reducing slow response action potential amplitude (SAPA), in reducing maximum upstroke velocity ($V_{max}$) and in reducing tone of rabbit aorta by high potassium (Vasc. Ca$^{++}$ Block)

| Compound | IC$_{50}$ (M) | | |
|---|---|---|---|
| | SAPA | $V_{max}$ | Vasc. Ca$^{++}$ Block |
| Ex. 1 | >>1 · 10$^{-5}$ | 6.7 0.1 · 10$^{-6}$ | 1.6 0.1 · 10$^{-6}$ |
| Ex. 3 | 1.5 ± 0.1 · 10$^{-6}$ | 3.8 ± 0.04 · 10$^{-6}$ | 1.7 ± 0.1 · 10$^{-6}$ |
| Ex. 24 | 2.6 ± 0.18 · 10$^{-6}$ | — | 1.2 ± 0.1 · 10$^{-6}$ |

TABLE 3

Effect of Examples 1 and 3 on normal action potential parameters in isolated canine cardiac Purkinje fibers

| Compound | RP | PP | $V_{max}$ | APD$_{50}$ | APD$_{90}$ |
|---|---|---|---|---|---|
| Ex. 1 | | | | | |
| Pre-drug | 94 ± 1 | 35 ± 1 | 520 ± 11 | 252 ± 3 | 336 ± 3 |
| 1 × 10$^{-6}$ | 94 ± 1 | 35 ± 1 | 443 ± 7* | 219 ± 3* | 320 ± 3 |
| 3 × 10$^{-6}$ | 89 ± 1 | 28 ± 1* | 375 ± 11* | 154 ± 3* | 305 ± 4 |
| 1 × 10$^{-5}$ | 89 ± 1 | 11 ± 2* | 203 ± 19* | 160 ± 3* | 320 ± 3 |
| Ex. 3 | | | | | |
| Pre-drug | 94 ± 1 | 34 ± 1 | 520 ± 18 | 258 ± 5 | 319 ± 4 |
| 1 × 10$^{-6}$ | 88 ± 1* | 32 ± 1 | 401 ± 16* | 181 ± 5* | 282 ± 2* |
| 3 × 10$^{-6}$ | 88 ± 1* | 26 ± 1* | 286 ± 9* | 125 ± 3* | 251 ± 1* |
| 1 × 10$^{-5}$ | 84 ± 1* | 7 ± 1* | 156 ± 11* | 123 ± 2* | 271 ± 8* |

*Signifies differences from pre-drug values to be significantly different (p <0.05)
RP = resting potential.
PP = peak potential.
$V_{max}$ = velocity of upstroke.
APD$_{50}$ = action potential duration @ 50% repolarization.
APD$_{90}$ = action potential duration @ 90% repolarization.

EXAMPLE 35

Antiarrhythmic activity was confirmed for the compound of Example 1 using a standard canine arrhythmia model as reported in J. L. Bergey et al., "Antiarrhythmic, hemodynamic, and cardiac electrophysiological evaluation of N-(2,6-dimethylphenyl)-N'-[3-(1-methylethylamino)propyl]urea), (Wy 42,362)", Arzneim.-Forsch. 33:1258, 1983). In dogs suffering from 24 hour post-infarction arrhythmias the compound of Example 1 reversed arrhythmias in 5 out of 5 dogs tested following intravenous doses ranging from 6 to 15 mg/kg.

What is claimed is:

1. A method for the treatment of myocardial ischemia and arrhythmia comprising administering to a mammalian specie in need thereof a therapeutically effective amount of a compound having the formula

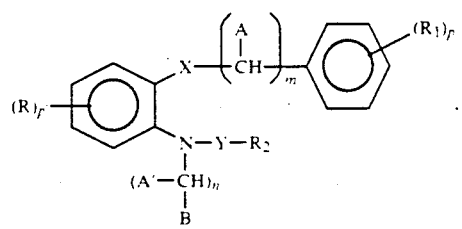

and to acid addition salts and quaternary ammonium salts thereof, wherein

R and R$_1$ each independently represent hydrogen, halo, lower alkyl, lower alkoxy, trihalomethyl, nitro, amino or hydroxy;

X represents oxa (—O—) or thia (—S—);

B represents a basic nitrogen-containing radical of the formula

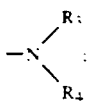

A and A' are independently selected from hydrogen or lower alkyl;
m is zero or an integer from 1 to 3;
n represents an integer from 2-5;
p and p' are the same or different integer of 1 to 3;

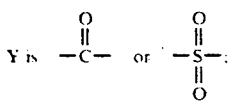

$R_2$ is lower alkyl, aryl, aralkyl, cycloalkyl(lower alkyl), lower alkenyl, lower alkadienyl, α-substituted phenyl alkyl, aralkenyl, aralkynyl or heteroaryl; and $R_3$ and $R_4$ are independently selected from hydrogen, lower alkyl, hydroxy lower alkyl, R substituted phenyl lower alkyl, R substituted cinnamoyl, 2- or 4-pyridylaklyl, and N-(lower alkyl)phenyl-(lower alkyl); or $R_3$ and $R_4$ taken together with the nitrogen atom to which they are attached form a 5- to 7-membered monocyclic heterocycle which may contain one oxygen atom or one additional nitrogen atom and which heterocycle may be substituted by 1, 2 or 3 lower alkyl, lower alkoxy, hydroxy lower alkyl or lower alkanoyloxy-lower alkyl groups.

2. The method of claim 1 wherein in said compound
R is hydrogen, methoxy or Cl;
$R_1$ is hydrogen, methoxy or Cl;
A is hydrogen or methyl;
A' is hydrogen or methyl;

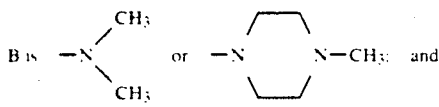

—Y—$R_2$ is phenylacetyl or cinnamoyl.

3. The method of claim 1 wherein in said compound
R is hydrogen;
$R_1$ is methoxy;
A and A' are each hydrogen;
m, p and p' are each 1;
n is 3;

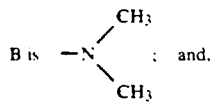

—Y—$R_2$ is phenylacetyl.

4. The method of claim 1 wherein said compound has the name N-[2-[[(4-chlorophenyl)methyl]thio]phenyl]-N-[3-(dimethylamino)propyl]benzeneacetamlde.

5. The method of claim 1 wherein said compound has the name N-[3-(dimethylamino)propyl]-N-[2-[[(4-methoxyphenyl)methyl]thio]phenyl]benzeneacetamide, monohydrochloride.

6. The method of claim 1 wherein said compound has the name N-[3-(dimethylamino)propyl]-N-[2-[(phenyl-methyl)thio]phenylbenzeneacetamide, monohydrochloride.

7. The method of claim 1 wherein said compound has the name N-[2-(dimethylamino)ethyl]-N-[2-[(phenylmethyl)-thio]phenyl]benzeneacetamide, monohydrochloride.

8. The method of claim 1 wherein said compound has the name N-[4-(dimethylamino)butyl]-N-[2-[(phenylmethyl)thio]phenyl]benzeneacetamide oxalate (1:1) salt.

9. The method of claim 1 wherein said compound has the name N-[3-(dimethylamino)propyl]-N-[2-(phneylmethoxy)-phenyl]benzeneacetamide, oxalate salt (1:1).

10. The method of claim 1 wherein said compound has the name 2'-(benzyl-thio)-N-[3-(dimethylamino)-propyl]-benzanilide, hydrochloride.

11. The method of claim 1 wherein said compound has the name N-[3-(dimethylamino)propyl]-N-[4,5-dimethoxy-2-[(phenylmethyl)thio]phenyl]benzeneacetamide, (1:1) salt.

12. The method of claim 1 wherein said compound has the name N-[3-(dimethylamino)propyl]-N-[4-chloro-2-[[(4-methoxyphenyl)methyl]thio]phenyl]benzeneacetamide, monohydrochloride.

13. The method of claim 1 wherein said compound has the name N-[2-(dimethylamino)ethyl]-N-2-[[(4-methoxyphenyl)methyl]thio]phenyl]-3-phenyl-2-propenamide, monohydrochloride.

14. The method of claim 1 wherein said compound has the name N-[2-(dimethylamino)ethyl]-3-phenyl-N-[2-[(phenylmethyl)thio]phenyl]-2-propenamide, monohydrochloride.

15. The method of claim 1 wherein said compound has the name 2'-(benzylthio)-4-chloro-N-[3-(dimethylamino)propyl]-benzanilide, hydrochloride.

16. The method of claim 1 wherein said compound has the name 2'-(benzylthio)-N-[3-(dimethylamino)-propyl]isonicotinanilide, hydrochloride, hydrate (1:2:1).

17. The method of claim 1 wherein said compound has the name N-[2-(dimethylamino)ethyl]-N-[2-[(phenylmethyl)thio]-4-(trifluoromethyl)phenyl]-2-propenamide, monohydrochloride.

18. The method of claim 1 wherein said compound has the name N-[2-(dimethylamino)ethyl]-3-phenyl-N-[2-[(2-(phenylethyl)thio]phenyl]-2-propenamide, monohydrochloride.

19. The method of claim 1 wherein said compound has the name N-[2-(dimethylamino)ethyl]-3-phenyl-N-[2-(phenylmethoxy)phenyl]-2-propenamide, monohydrochloride.

20. The method of claim 1 wherein said compound has the name N-[2-(dimethylamino)ethyl]-3-phenyl-N-[2-[(1-phenylethyl)thio]phenyl]-2-propenamide, monohydrobromide.

21. The method of claim 1 wherein said compound has the name N-[2-(dimethylamino)ethyl]-N-[2-[(phenylmethyl)thio]phenyl]benzamide, monohydrochloride.

22. The method of claim 1 wherein said compound has the name N-[2-(dimethylamino)ethyl]-α-oxo-N-[2-[(phenylmethyl)thio]phenyl]benzeneacetamide, monohydrochloride.

23. The method of claim 1 wherein said compound has the name N-[2-(dimethylamino)ethyl]-α-hydroxy-N-[2-[(phenylmethyl)thio]phenyl]benzeneacetamide, monohydrochloride.

24. The method of claim 1 wherein said compound has the name N-[3-(dimethylamino)propyl]-N-[2-

[(phenylmethyl)thio]-phenyl]benzenepropanamide, monohydrobromide.

25. The method of claim 1 wherein said compound has the name N-[3-(dimethylamino)propyl]-N-[2-(phenylmethyl)thio]-phenyl]hexanamide, monohydrochloride.

26. The method of claim 1 wherein said compound has the name N-[3-(dimethylamino)propyl]-3-phenyl-N-[2-[(phenylmethyl)thio]phenyl]-2-propynamide, oxalate salt (1:1).

27. The method of claim 1 wherein said compound has the name N-[4-(dimethylamino)butyl]-3-phenyl-N-[2-[(phenylmethyl)thio]phenyl]-2-propenamide, oxalate salt (1:1).

28. The method of claim 1 wherein said compound has the name N-[3-(dimethylamino)propyl]-4-methoxy-N-[2-[(phenylmethyl)thio]phenyl]benzeneacetamide, monohydrochloride.

29. The method of claim 1 wherein said compound has the name N-[5-(dimethylamino)pentyl-3-phenyl-N-[2-[(phenylmethyl)thio]phenyl]-2-propenamide.

30. The method of claim 1 wherein said compound has the name N-[3-(dimethylamino)propyl]-N-[2-[(phenylmethyl)thio]phenyl]cyclohexaneacetamide monohydrochloride.

31. The method of claim 1 wherein said compound has the name α-(acetyloxy)-N-[3-(dimethylamino)propyl]-N-[2-[(phenylmethyl)thio]phenyl]benzeneacetamide, monohydrochloride.

32. The method of claim 1 wherein said compound has the name N-[3-(dimethylamino)propyl]-3-phenyl-N-[2-(phenylmethoxy)phenyl]-2-propenamide, monohydrochloride.

33. The method of claim 1 wherein said compound has the name N-[3-(dimethylamino)propyl]-N-[2-(phenylthio)-phenyl]-benzeneacetamide, monohydrobromide.

34. The method of claim 1 wherein said compound has the name 4-chloro-N-[3-(dimethylamino)propyl]-N-[2-(phenylmethyl)thio[phenyl]-benzeneacetamide, monohydrochloride.

35. The method of claim 1 wherein said compound has the name -N-[3-(dimethylamino)propyl]-N-[2-(phenylmethyl)thio[phenyl]-benzenemethansulfonamide, monohydrochloride.

36. The method of claim 1 employed for the treatment of myocardial ischemia.

37. The method of claim 1 employed for the treatment of arrhythmia.

38. The method of claim 1 employed for the treatment of myocardial ischemia and arrhythmia.

* * * * *